(12) United States Patent
Arnitz

(10) Patent No.: US 9,039,638 B2
(45) Date of Patent: May 26, 2015

(54) TEST UNIT FOR CARRYING OUT A ONE-TIME TESTING OF A BODY FLUID

(75) Inventor: Theo Arnitz, Waghäusel (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1281 days.

(21) Appl. No.: 11/773,224

(22) Filed: Jul. 3, 2007

(65) Prior Publication Data

US 2008/0097244 A1  Apr. 24, 2008

Related U.S. Application Data

(63) Continuation of application No. PCT/EP2006/000385, filed on Jan. 18, 2006.

(30) Foreign Application Priority Data

Jan. 19, 2005  (DE) .......................... 10 2005 003 789

(51) Int. Cl.
*A61B 5/15* (2006.01)
*A61B 5/151* (2006.01)

(52) U.S. Cl.
CPC ........... *A61B 5/1411* (2013.01); *A61B 5/15142* (2013.01); *A61B 5/15186* (2013.01); *A61B 2562/247* (2013.01)

(58) Field of Classification Search
CPC ............. A61B 5/1411; A61B 5/15142; A61B 5/15186; A61B 2562/24; A61B 2562/242; A61B 2562/247
USPC ........................................................ 600/583
See application file for complete search history.

(56) References Cited

U.S. PATENT DOCUMENTS

| 2,208,606 | A | 7/1940 | Smith | |
|---|---|---|---|---|
| 2,217,602 | A | 10/1940 | Smith | |
| 5,374,250 | A | 12/1994 | Dixon | |
| 6,540,675 | B2 * | 4/2003 | Aceti et al. | 600/575 |
| 7,396,334 | B2 * | 7/2008 | Kuhr et al. | 600/583 |
| 2002/0087056 | A1 | 7/2002 | Aceti et al. | |
| 2002/0103499 | A1 | 8/2002 | Perez et al. | |

(Continued)

FOREIGN PATENT DOCUMENTS

| DE | 101 42 232 A1 | 3/2003 |
|---|---|---|
| DE | 102 58 016 A1 | 6/2004 |
| EP | 0 199 484 | 10/1986 |

(Continued)

OTHER PUBLICATIONS

Search Report for International Application No. PCT/EP2006/00385 mailed Jun. 14, 2006.

(Continued)

*Primary Examiner* — Lee S Cohen
*Assistant Examiner* — Emily Lloyd
(74) *Attorney, Agent, or Firm* — Woodard, Emhardt, Moriarty, McNett & Henry LLP

(57) ABSTRACT

A test unit for carrying out blood analysis includes a lancing element that can be pricked into a body part which has a capillary channel for transporting the body fluid that leads from a lancing member to a target site. A pretensioned distal sterile cover and a liquid permeable proximal sterile cover are proposed for the lancing element that is advantageously formed as a deep-drawn component.

11 Claims, 3 Drawing Sheets

(56) References Cited

U.S. PATENT DOCUMENTS

2003/0175323 A1* 9/2003 Utterberg et al. ............ 424/423
2012/0215084 A1* 8/2012 Douglas et al. ............... 600/347

FOREIGN PATENT DOCUMENTS

| EP | 1 491 143 A1 | 12/2004 |
| WO | WO 97/42882 | 11/1997 |
| WO | WO 99/55232 | 11/1999 |
| WO | WO 00/40150 | 7/2000 |
| WO | WO 2004/041088 | 5/2004 |
| WO | WO 2004/091403 | 10/2004 |
| WO | WO 2005/001418 | 1/2005 |
| WO | WO 2006/077080 | 7/2006 |

OTHER PUBLICATIONS

DE 102 58 016 A1 English Language Abstract.
EP 1 491 143 A1 English Language Abstract.
PCT/EP2006/000385 English Translation of International Preliminary Report on Patentability issued Jul. 24, 2007.

* cited by examiner

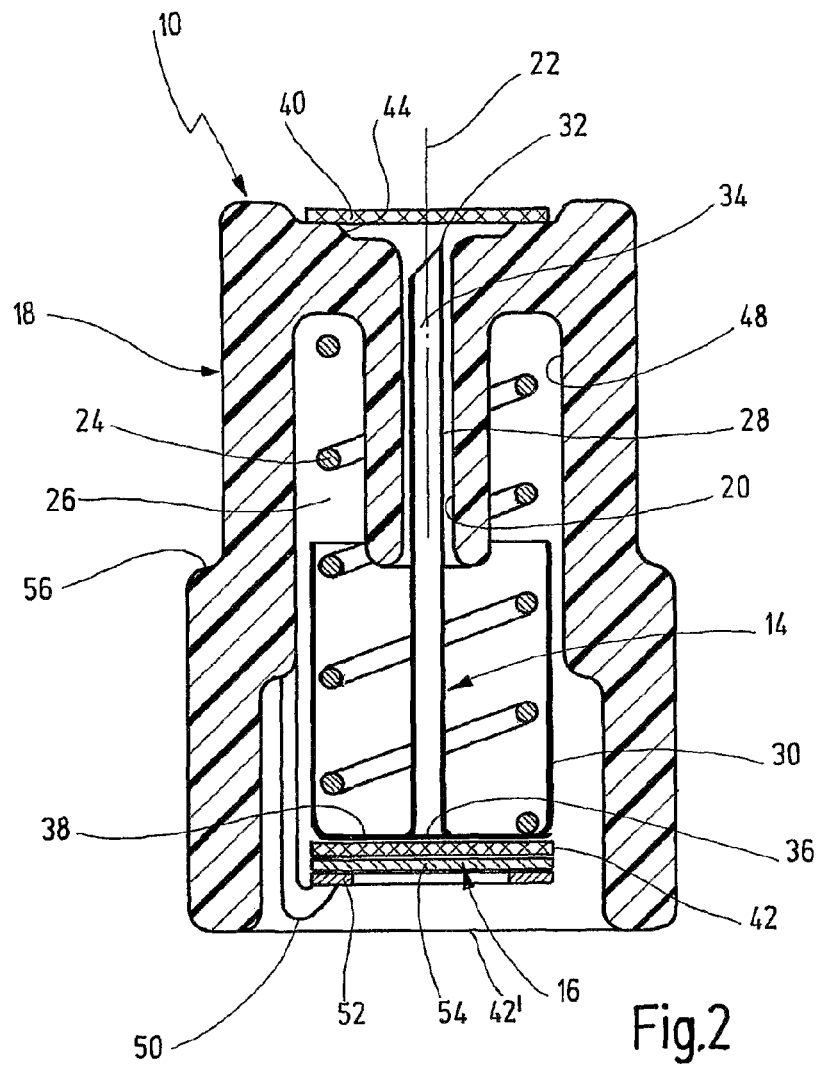
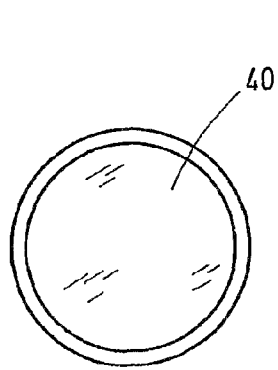
Fig.3a
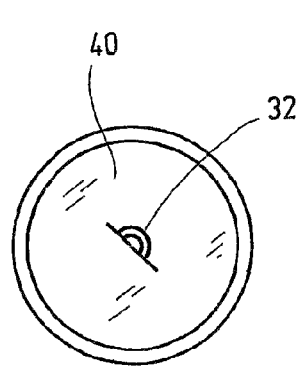
Fig.3b
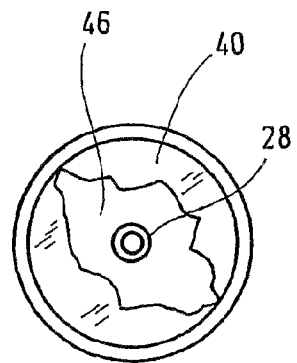
Fig.3c

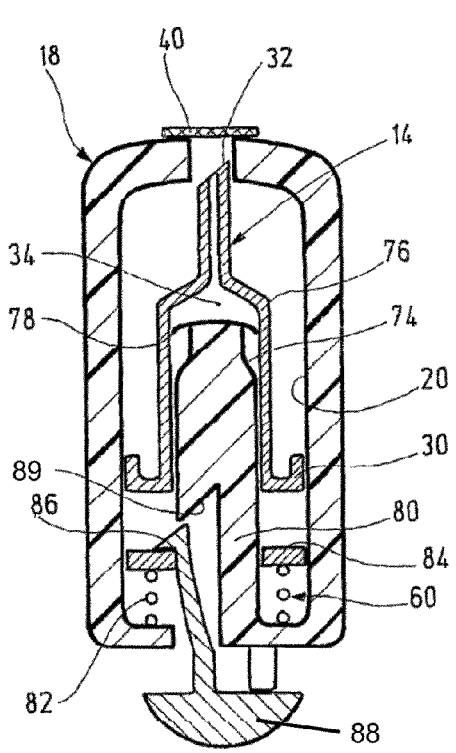
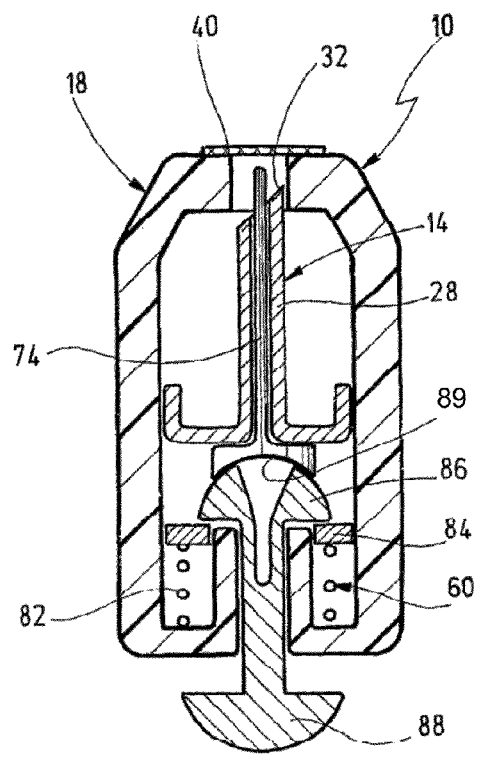
Fig.4  Fig.5
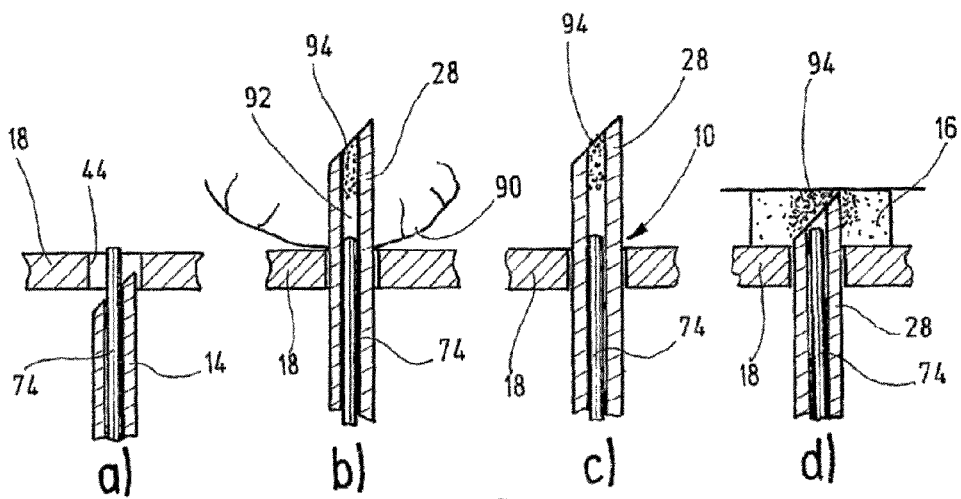
Fig.6

TEST UNIT FOR CARRYING OUT A ONE-TIME TESTING OF A BODY FLUID

CROSS-REFERENCE TO RELATED APPLICATIONS

This application is a continuation of International Patent Application No. PCT/EP2006/000385, filed Jan. 18, 2006, which claims the benefit of German Patent Application No. 10 2005 003 789.5 filed Jan. 19, 2005, which are incorporated by reference.

BACKGROUND

The invention concerns a test unit for carrying out one-time analyses in a body fluid, in particular blood, comprising a lancing element that can be pricked into a body part which has a capillary channel for transporting the body fluid that leads from a lancing member to a target site. In addition a production process for a test unit is stated.

Test units of this type especially for near patient glucose measuring systems are used to self-monitor the current blood sugar values of a user. In this connection integrated systems have already been proposed in which the functions "lancing" to collect capillary blood and "detecting" the glucose content have been combined in a user-friendly manner as a "single-test kit". Blood obtained in situ at the lancing site usually has to be collected by capillary transport and brought into contact with a test chemistry. In this process the lancing pain should be kept as low as possible and a hygienic handling should be ensured. Problems are caused by the complexity of such systems and the complicated manufacturing process.

SUMMARY

On this basis the object of the invention is to avoid the disadvantages occurring in the prior art and to improve a generic product and a production process in such a manner that mass production using an advantageous process sequence is also possible.

The combination of features stated in the independent claims is proposed to achieve this object. Advantageous embodiments and further developments of the invention are derived from the dependent claims.

Accordingly a sterile cover for the lancing element which is pretensioned and when being pierced uncovers a passage opening is proposed according to a first variant of the invention. This enables at least hygienically relevant areas of the lancing element to be screened from the entry of germs or other contaminants. The pretensioning of the cover can also be used to abruptly uncover a passage opening under point loading or by the lancing member during the lancing process with a low energy input similar to a bursting balloon. This prevents an undesired blunting of the lancing member. Moreover, it prevents the formation of hygienically problematic particles and punching residues when the sterile cover is pierced. Conversely it also reduces the risk of contamination by wiped off blood. Another advantage is that a simple visual check during manufacture suffices since even small defects or holes lead to a failure of the cover. The sterile barrier according to the invention can be used for simple open channel flat lancets and also for more complex shaped lancing components.

For an automatic opening during the lancing process, the sterile cover should be arranged distally in front of the lancing member i.e. at the front facing the body.

An advantageous embodiment provides that the sterile cover is formed by an elastic pretensioned tear-membrane. Alternatively the sterile cover can also be formed by a shrink membrane that is tensioned by the action of heat.

The inner width of the uncovered passage opening should be larger and preferably several times larger than the piercing cross-section of the lancing element so that during retraction no blood is wiped off on the pierced foil that could contaminate the system.

Another important aspect of the invention is the use of a sterile cover for the lancing element which is at least partially permeable to the body fluid. This enables a sterile barrier to be created on the side facing away from the body when in use which at the same time ensures a capillary coupling for liquid transport to an (unsterile) test field.

The liquid-permeable sterile cover is advantageously arranged proximally after the lancing element. In this case it is advantageous when the sterile cover is surface-connected to a section of the lancing element. In doing so it should at least be ensured that the sterile cover spans an orifice cross-section of the capillary channel.

A liquid-permeable sterile barrier can be created by means of the fact that the sterile cover functions like a germ filter that seals against the passage of germs. In an advantageous embodiment the sterile cover is formed by a sterile-tight filter fleece.

Also for the manufacturing it is technically advantageous when the sterile cover covers an opening of a receiving part for the lancing element.

Another aspect of the invention is that the lancing element is formed by a one-piece, deep-drawn component. This allows precise multifunctional shaped parts to be realized which, in addition to the lancing function, also allow additional options with regard to liquid transport, sterile sealing, holding etc.

The lancing element is advantageously deep-drawn from a ductile material, preferably stainless steel sheet metal, which optionally contains anti-bacterial components such as silver or iodine.

Other advantageous embodiments provide that the lancing element has a hollow cannula and a radially projecting flange at the proximal end of the hollow cannula.

For the manufacturing process it is also advantageous when the lancing element is arranged in a receiving part preferably designed as an injection-moulded part.

The lancing process is simplified when the receiving part has a push guide for the lancing element running in the lancing direction. For an automatic return movement it is advantageous when a return spring that is pretensioned during the lancing advance movement of the lancing element is arranged between the receiving part and the lancing element.

The receiving part advantageously has form-locking means to hold it in a form-locking manner in a housing.

A detection element for detecting an analyte in the body fluid to which body fluid can be applied via the capillary channel is provided for an integrated system.

Further improvements are achieved by means of the fact that the detection element has a measuring field extending transversely to the lancing direction and that the detection element is coupled with the lancing element by connecting means and in particular latching means and is arranged on a rear side of the liquid-permeable sterile cover which faces away from the lancing element.

Yet another important aspect of the invention is that a plunger is arranged in the lancing element designed as a hollow cannula. This enables the uptake and dispensing of the liquid sample to be directly supported in a simple manner.

This advantageously takes place by means of the fact that the hollow cannula can be moved relative to the plunger so that body fluid is sucked into the channel and/or displaced therefrom. Another improvement is achieved by means of the fact that the plunger seals a cross-section of the channel preferably by means of a circumferential seal.

In order to enable the relative movement in a simple manner it is advantageous when the plunger is connected with a receiving part for the lancing element in a non-displaceable manner wherein the receiving part forms a push guide for the lancing element.

The test units according to the invention are advantageously operated in such a manner that the lancing element is driven by a lancing drive at least in an advance movement for insertion into the body part. In this connection it is sufficient for a microfluidic system when the lancing element has a limited collection volume for body fluid of less than 100 microliters, preferably of less than 10 microliters.

With regard to the process, the object mentioned above is achieved in that the lancing element is incorporated into the receiving part in an unsterile environment and is covered by a sterile cover, the receiving part containing the integrated lancing element is then preferably sterilized by X-ray irradiation and subsequently the detection element is inserted in an unsterile manner.

BRIEF DESCRIPTION OF THE DRAWINGS

The invention is further elucidated in the following on the basis of the embodiment example shown schematically in the drawing.

FIG. 2 shows the test unit in an axial section that is enlarged compared to FIG. 1;

FIG. 3a to 3c show a top-view of a sterile cover of the test unit in various positions of advance of an integrated lancing element;

FIGS. 4 and 5 show further embodiments of a test unit with an integrated needle plunger and FIG. 6 shows the test unit of FIG. 5 in various phases of liquid collection in a cut-out partial view.

DESCRIPTION OF SELECTED EMBODIMENTS

Figure 1:
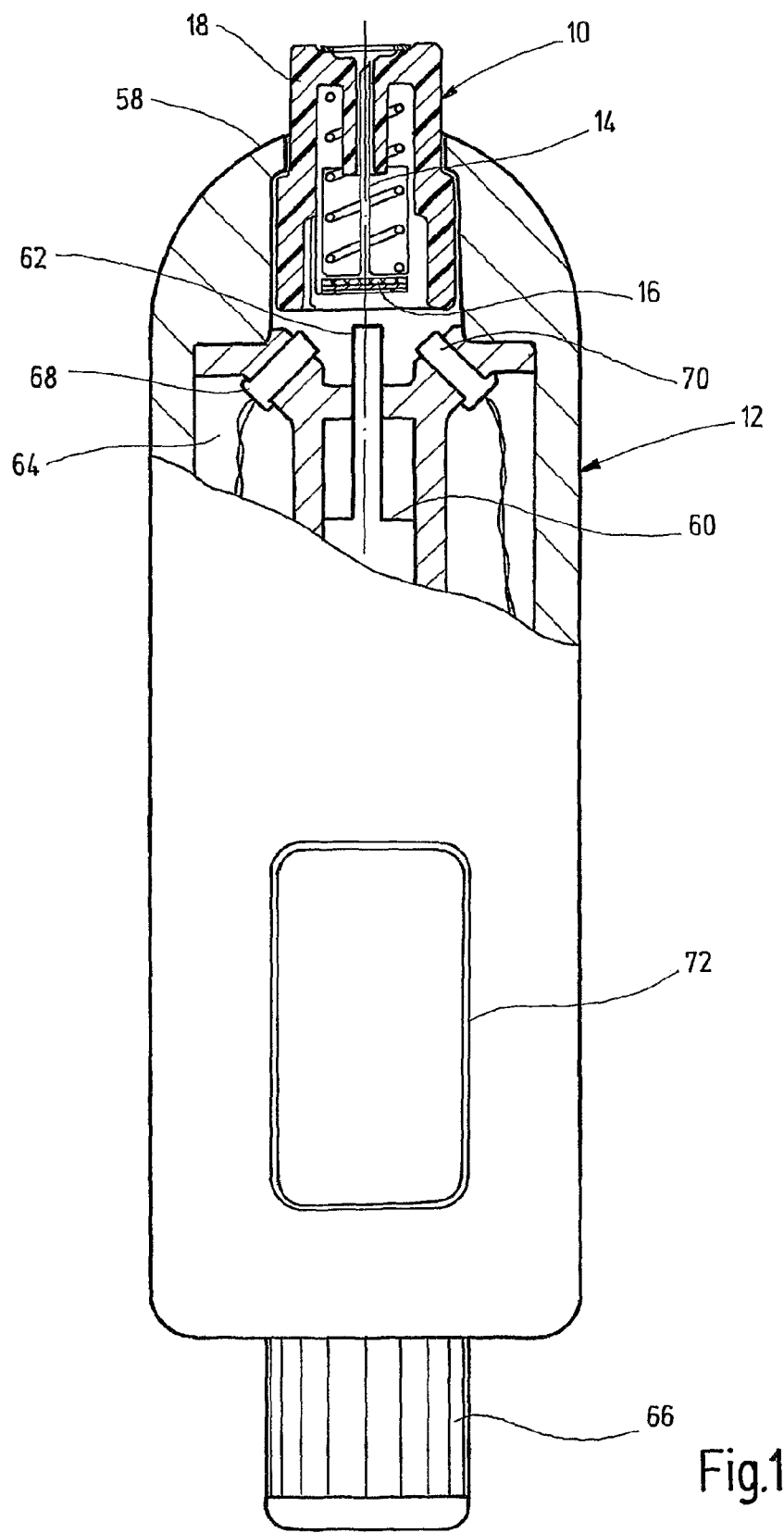
FIG. 1 shows a hand-held device for blood glucose analyses with a disposable test unit inserted therein in a partial cut-out view.

The test unit 10 shown in the drawing can be used as a disposable single-use component in a hand-held device 12 in order to enable near-patient blood analyses for glucose monitoring with the integrated lancing element 14 and detection element 16.

As best shown in FIG. 2, the test unit 10 has a housing-like receiving part 18 for the lancing element 14. In this case the receiving part 18 forms a push guide 20 in which the lancing element 14 is guided linearly in the direction of a lancing axis 22 for a reciprocating lancing movement. The return movement occurs under the force of a return spring 24 which is pretensioned in a spring cage 26 between the lancing element 14 and the receiving part 18.

The lancing element 14 is formed by a one-piece, deep-drawn component made of stainless steel metal sheet. It comprises a hollow cannula 28 and a flange sleeve 30 moulded proximally thereon. The bevelled distal end of the hollow cannula 28 forms a pointed lancing member 32 for insertion into a body part of a test subject. The inside of the hollow cannula 28 serves as a capillary channel 34 for blood transport supported by capillary force from the lancing member 32 to a proximal central aperture 36 on the radially projecting front collar 38 of the flange sleeve 30.

In order to be able to screen at least the hollow cannula 28 of the lancing element 14 against the penetration of germs and other contaminants in a sterile-tight manner, two sterile covers 40, 42 are provided. The first or distal sterile cover 40 is located in front of the lancing member 32 in relation to the lancing or advancing direction and spans a free outlet cross-section 44 of the receiving part 18, whereas the second or proximal sterile cover 42 covers the channel mouth 36 in a sterile-tight manner. It is basically also possible that a sterile cover 42' covers the proximal or drive-side opening of the receiving part 18.

In order to optimize the lancing process also from a hygienic point of view, the distal sterile cover 40 is formed by an elastic pretensioned tear-membrane. As shown in FIG. 3 this membrane 40 bursts abruptly when it is punctured by the lancing member 32 due to the point load (FIG. 3b) and exposes a large passage opening 46 for the passage of the hollow cannula 28 (FIG. 3c). In this manner it can prevent an unintentional contamination of the body with membrane particles and punching residues. Conversely it also reliably prevents blood from being wiped off and resulting in unintentional contamination when the cannula 28 is pulled back.

The proximal sterile cover 42 lies flat against the front collar 38 of the flange sleeve 30. This enables a fluidic connection of the capillary channel 34 with the detection element 16 by means of a fleece material. This material is permeable at least to constituents of the blood fluid and in particular to plasma but prevents passage of germs depending on the type of sterile filter. A fibre fleece is expediently used for the sterile cover 42. For an additional germ seal the flange sleeve 30 should be mounted in the bore 48 of the receiving part 18 with as little guide play as possible. In addition there is also the option of providing the lancing element 14 with anti-bacterial substances such as silver or iodine.

The detection element 16 is held on the rear side of the sterile cover 42 facing away from the lancing element 14 by means of a latching hook 50 in a plane-fitting arrangement. For this purpose the detection element 16 has a clamping ring 52 which is glued on the edge of a disk-shaped measuring field 54. The measuring field 54 can contain a detection reagent which responds to glucose in the supplied blood fluid for example by a colour change. The described fastener aligns the measuring field 54 orthogonally to the lancing axis 22 such that a reflection photometric evaluation in the longitudinal direction of the device is possible.

The receiving part 18 can be formed from plastic as an injection-moulded component. In this connection it is possible that the distal sterile cover 40 also consists of an injection-moulded material or is already mounted on the front of the receiving part 18 during the injection-moulding. It is also conceivable that the return spring 24 can also be extruded from plastic. In order to centre the receiving part 18 in the device 12, it is provided with a stop shoulder 56 which can engage in a form-fitting manner with a complementary contour on the device housing 58 as shown in FIG. 1. The device 12 has a lancing drive 60 the plunger 62 of which abuts against the clamping ring 52 as an abutment by means of radial holding knobs (not shown). The return spring 24 presses the front collar 38 of the lancing element 14 against the proximal cover element 42 and presses this element against the measuring field 54 to ensure a capillary coupling for blood transport.

The receiving part 18 can be clamped in an air-tight manner in the housing 58 by means of a seal that is not shown and as a result of which negative pressure relative to the atmosphere can be applied to the sealed inner space 64 of the housing. This can for example be achieved by constructing the rear trigger 66 of the lancing drive 60 like a pipette in order to thus, on actuation, assist blood collection and blood transport in the capillary channel 28 by the negative pressure that is formed.

After the lancing process the glucose detection can take place in a contact-free manner by a photometer arrangement consisting of a light source 68 and light receiver 70 that is aligned with the measuring field 54. The measured result can then be shown to the user on a display 72 of the device 12. After the measurement is completed, the test unit 10 is removed from the housing 58 and discarded. It is basically also possible that the device 12 is only designed as applicator with a lancing driven whereas the evaluation, as well as optionally the storage and disposal, of the test units 10 is carried out in a separate system.

In the embodiment examples shown in FIGS. 4 to 6 the same parts are labelled with the same reference numerals as described above. According to FIG. 4 a plunger 74 is arranged in a widened section 76 of the lancing element 14. This plunger 74 is sealed by a sealing lip 78 against the wall of the channel 34 so that a relative movement of the lancing element 14 causes a change in pressure to suck or displace blood. For this purpose the plunger 74 is connected with the receiving part 18 in a secure manner against displacement by a connecting part 80 whereas the lancing element 14 is mounted in a linearly movable manner in the push guide 20. In this case the receiving part 18 contains the lancing drive 60 in the form of a pretensioned spring 82. The spring 82 is braced against a holding ring 84 in the distal direction which is held in its initial position by hook-like expanding catches 86. When the trigger 88 is actuated, the three catches 86 distributed in the circumferential direction slide into a corresponding bevel 89 of the plunger 74 which releases the holding ring 84 and, under spring force, drives the collar 30 of the lancing element 14 for insertion into the skin of the body part.

A similar actuating mechanism 86, 88 for the integrated spring drive 60 of the lancing element 14 is provided in the embodiment according to FIG. 5. In this case the plunger 74 engages as a pin through the entire length of the hollow cannula 28 in which case the permanent connection with the receiving part 18 is not shown for the sake of simplicity.

A blood analysis can proceed as shown in FIG. 6 by means of such a test element 10. In its initial position the lancing element 14 with the plunger 74 located therein is arranged in the receiving part 18 (FIG. 6a). The user places the receiving part 18 in the area of the outlet opening 44 onto a body part, especially a finger pad and then triggers the actuator 88. As a result the hollow cannula 28 is pricked into the tissue whereas the plunger 74 remains stationary and thus provides a negative pressure in the receiving volume 92 (FIG. 6b). The receiving volume is typically a few microliters. This receiving volume of a few microliters is due to the corresponding small needle dimensions, which in turn reduces the puncture pain and make the skin lesion small. After a short retention period sufficient blood 94 has collected in the holding volume 92 and the entire arrangement of the test unit 10 consisting of the receiving part 18 and lancing element 14 can be pulled by the user out of the body part 90 and transferred to an analytical unit (FIG. 6c) (not shown) while retaining the relative position. The analytical unit comprises a test or detection element 16 having a test chemistry that responds to the analyte (glucose) in the blood sample 94. As shown in FIG. 6d, the user presses the distal end of hollow cannula 28 against the detection element 16 as a result of which the spring 82 under compression enables a return movement of the plunger 74 thus ensuring a corresponding displacement of the amount of blood taken up. Subsequently the test unit 10 can be discarded while the analysis is carried out automatically.

When the test units are produced as a mass product with an integrated collection and detection system, the required sterilization of the lancing element is difficult to accomplish in the presence of radiation-sensitive test reagents on the detection element. A solution to this process problem is therefore a multistep process sequence. Firstly the lancing element 14 is preassembled in the receiving part in an unsterile environment whereby at least the capillary channel 34 is isolated by the sterile covers 40, 42. Then a gamma sterilization takes place where the lancing element and deep-drawn component 14 remain in a sterile enclosure. Subsequently the unsterile detection element 16 can be inserted so that overall sterile conditions can be dispensed with for the process management.

What is claimed is:

1. A test unit, comprising:
   a lancing element configured to prick a body part, wherein the lancing element has a capillary channel for transporting a body fluid that leads from the lancing element to a target site; and
   a sterile cover arranged in front of the lancing element, wherein the cover is pretensioned to burst when pierced to create a passage opening in the cover, wherein the cross-section of the passage opening is several times larger than the piercing cross-section of the lancing element, wherein the passage opening is configured to prevent wiping of blood onto the sterile cover during retraction of the lancing element, wherein the sterile cover is formed by an elastic pretensioned tear-membrane.

2. The test unit according to claim 1, further comprising:
   a detection element configured to detect an analyte in the body fluid to which body fluid can be applied via the capillary channel.

3. The test unit according to claim 2, further comprising a receiving part in which the lancing element is disposed.

4. The test unit according to claim 3, wherein the receiving part has a push guide in which the lancing element is guided.

5. The test unit according to claim 3, further comprising a return spring arranged between the receiving part and the lancing element, wherein the return spring is configured to be tensioned during a lancing advance movement of the lancing element.

6. The test unit according to claim 3, wherein the receiving part has a stop shoulder to hold the receiving part in a form-fitting manner in a housing.

7. The test unit according to claim 2, wherein the detection element has a measuring field extending transversely to the lancing element.

8. The test unit according to claim 2, wherein the detection element is coupled with the lancing element by a latching hook.

9. The test unit according to claim 2, further comprising a plunger arranged in the capillary channel of the lancing element.

10. The test unit according to claim 1, wherein the lancing element has a pointed lancing member, wherein the capillary channel is configured to transport the blood via capillary action from the pointed lancing member to a proximal central aperture, wherein the lancing element has a radially projecting front collar at the proximal central aperture.

11. A test unit, comprising:
    a receiving part having a free outlet opening;
    a lancing element received in the receiving part, the lancing element including a capillary channel, the lancing element having a pointed lancing member, the capillary channel being configured to transport blood via capillary action from the pointed lancing member to a proximal central aperture, the lancing element having a radially projecting front collar at the proximal central aperture;

a distal sterile cover spanning the free outlet opening in a sterile-tight manner to protect the lancing element from contaminants, wherein the distal sterile cover is an elastic pretensioned tear-membrane that is pretensioned to burst abruptly and create a large passage opening in the membrane for passage of the lancing element, wherein the large passage in the membrane has a cross-section that is several times larger than a piercing cross-section of the lancing element, wherein the passage opening is configured to prevent wiping of blood off onto the membrane during retraction of the lancing element;

a proximal sterile cover lying flat against the front collar of the lancing element, the proximal sterile cover covering the proximal central aperture of the lancing element, the proximal sterile cover being made of fiber fleece that is permeable to the blood, wherein the fiber fleece is configured to prevent passage of germs;

a detection element positioned on a rear side of the proximal sterile cover, wherein the rear side of the proximal cover faces away from the lancing element, the detection element having a measuring field with a reagent for analyzing the blood; and a return spring arranged between the lancing element and the receiving part, wherein the return spring presses the front collar of the lancing element against the proximal sterile cover, wherein the return spring via the front collar further presses the proximal sterile cover against the measuring field to ensure capillary coupling for transporting the blood.

* * * * *